United States Patent [19]

Mochida et al.

[11] Patent Number: 4,968,680
[45] Date of Patent: * Nov. 6, 1990

[54] 1-ACYL-2,3-DIHYDRO-4(1H)-QUINOLINONE-4-OXIME DERIVATIVES, PROCESS FOR PRODUCING THEM AND USE THEREOF

[75] Inventors: Ei Mochida, Tokyo; Akio Uemura; Kazuo Kato, both of Mishima; Hiroki Tokunaga, Kita; Akinori Haga, Kawasaki, all of Japan

[73] Assignees: Mochida Pharmaceutical Co., Ltd.; Hodogaya Chemical Co., Ltd., both of Tokyo, Japan

[*] Notice: The portion of the term of this patent subsequent to Jun. 13, 2006 has been disclaimed.

[21] Appl. No.: 264,017

[22] Filed: Oct. 28, 1988

[30] Foreign Application Priority Data

Oct. 31, 1987 [JP] Japan .................. 62-276474

[51] Int. Cl.$^5$ .................. A61K 31/505; A61K 31/47; A61K 31/495
[52] U.S. Cl. .................. 514/243; 514/256; 514/311; 514/313; 514/314; 544/224; 544/238; 544/333; 544/335; 546/159; 546/168; 546/172
[58] Field of Search .................. 546/159, 168, 172; 544/224, 238, 333, 335; 514/311, 313, 314, 253, 256

[56] References Cited

U.S. PATENT DOCUMENTS

| | | | |
|---|---|---|---|
| 3,976,650 | 8/1976 | Johnson | 260/287 K |
| 4,013,662 | 3/1977 | Harbert | 260/287 K |
| 4,260,764 | 4/1981 | Johnson | 546/153 |
| 4,421,919 | 12/1983 | Jinbo et al. | 544/159 |
| 4,440,770 | 4/1984 | Mochida et al. | 514/313 |
| 4,521,607 | 6/1985 | Oka et al. | 549/39 |
| 4,736,055 | 4/1988 | Dietliker et al. | 560/13 |
| 4,839,368 | 6/1989 | Mochinda et al. | 514/313 |

FOREIGN PATENT DOCUMENTS

| | | |
|---|---|---|
| 0163888 | 4/1985 | European Pat. Off. |
| 0180352 | 5/1986 | European Pat. Off. |
| 2487346 | 1/1982 | France |
| 2081091 | 2/1982 | United Kingdom |
| 8706580 | 11/1987 | World Int. Prop. O. ........ 546/159 |

OTHER PUBLICATIONS

Chemical Abstracts, vol. 87, No. 16, Oct. 17, 1977, Bekhli et al. "Use of IR Spectroscopy for studying the mechanism of B-(2-" etc., entry 87:133435p.
Chemical Abstracts, vol. 84, No. 1, Jan. 5, 1976, A. F. Bekhli et al. entry 84:4800t.
Chemical Abstracts, vol. 84, No. 89971x (1976) Hayashi et al.
Chemical Abstracts, vol. 85, No. 108503k (1976) JANZSO.
Chemical Abstracts, vol. 99, No. 54065N (1983) Moravcsik et al.
D. Misiti et al., Journal of Heterocyclic Chemistry, "1,2,3,5-Tetrahydro-4H-1, 5-benzodiazepin-4-ones and 1,2,3,4-Tetrahydro-5H-1, 4-benzodiazepin-5-ones from the Reaction of Hydrazoic Acid on 1,2,3,4-Tetrahydroquinolin-4-ones", 4/1971, pp. 231–236, vol. 8, No. 2.
G. Bradley et al., Journal of the Chemical Society, "2,3-Dihydroquinolin-4(1H)-ones, Part I, Halogen-substituted 2,3-Dihydroquinolin-4(1H)-ones and their 1-(2-Acylethyl) Derivatives", 1972, pp. 2019–2023.
T. Crabb et al., Journal of the Chemical Society, "Microbiological Transformations, Part 6. Microbiological Transformations of Acyl Derivatives of Indoline, 1,2,3,4-Tetrahydroquinoline, 1,2,3,4-Terrahydroisoquinoline and 2,3,4,5-Tetrahydro-1H-1-benzaepine with the Fungus Cunninghamella elegans", 1985, pp. 1381–1385.
Bekhli et al., Chem Abs. vol. 87 No. 16 entry 133435p (1977).
Bekhli et al., Chem Abs. vol. 84 No. 1 entry 4800t (1976).
Hayashi et al., Chem. Abs. vol. 84 entry 89971x (1976).
Janzso, Chem. Abs. vol. 85 entry 108503k (1976).
Moravcsik et al., Chem. Abs. vol. 99 entry 54065n (1983).
Misiti et al., J. Heb. Chem. vol. 8, No. 2 pp. 231–236 (1971).
Bradley et al., J. Chem. Soc. Perkin Trans. I (13) pp. 2019–2023 (1972).
Crabb et al., J. Chem. Soc. Perlein Trans. I (7) pp. 1381–1385 (1985).

*Primary Examiner*—Mukund J. Shah
*Assistant Examiner*—E. C. Ward
*Attorney, Agent, or Firm*—Oliff & Berridge

[57] ABSTRACT

The present invention relates to novel 1-acyl-2,3-dihydro-4(1H)-quinolinone-4-oxime-O-sulfonic acid compound, processes for producing said compounds, intermediate compounds to produce said compounds and compositions containing said compounds with potent diuretic activity that can be used for treating and/or preventing hypertension, oedema and/or for removing ascites.

The present invention is based on the selection of 1-acyl-7-halo-2,3-dihydro-4(1H)-quinolinone-4-oxime-O-sulfonic acid compounds, namely heterocyclic-or fused heterocyclic- carbonyl derivatives at 1 position.

The compounds of the present invention containing these substituents have potent hypotensive, antioedematous and diuretic effect as well as an activity to remove ascites and are extremely useful for the treatment of diseases and disorders mentioned above.

32 Claims, No Drawings

1-ACYL-2,3-DIHYDRO-4(1H)-QUINOLINONE-4-OXIME DERIVATIVES, PROCESS FOR PRODUCING THEM AND USE THEREOF

BACKGROUND OF THE INVENTION

The present invention relates to novel 1-acyl-2,3-dihydro-4(1H)-quinolinone-4-oxime-O-sulfonic acid compounds, process for producing said compounds, intermediate compounds, novel 1-acyl-2,3-dihydro4(1H)-quinolinone compounds, to produce said compounds and compositions containing said compounds with potent diuretic activity that can be used for treating and/or preventing hypertension, oedema and/or for removing ascites.

For the treatment of hypertension benzothiazide derivatives or so-called loop diuretics have been widely used to lower blood pressure. These agents act mainly on the distal part of renal tubule or the loop of Henle and increase renal excretion of electrolytes and water. Many of these diuretics, however, are known to show several adverse reaction in common, for example, hypokalemia, hyperuricemia, decrease in sugar tolerance and disorder in lipid metabolism.

Diuretic agents have also been used for the treatment of oedema resulting from retention of water and electrolytes based on cardiac or renal insufficiency or on metabolic disorders, but such conventionally used diuretics show only marginal efficacy against retention of ascites which is often observed in the patients with abdominal tumor or liver cirrhosis.

These benzothiazide diuretics and loop diuretics are known to share common chemical substructures.

From the foregoing background, it has been desired to develop novel diuretics that are useful in the treatment of hypertension, oedema and removal of ascites and that do not cause aforementioned adverse reactions by synthesizing compounds whose chemical structures are novel and different from those of known diuretics.

SUMMARY OF THE INVENTION

An object of the present invention is to provide novel 1-acyl-2,3-dihydro-4(1H)-quinolinone-4-oxime-O-sulfonic acid compounds and salts thereof, solvates of said compounds and solvates of said salts.

Another object of the present invention is to provide processes for producing novel 1-acyl-2,3-dihydro-4(1H)-quinolinone-4-oxime-O-sulfonic acid compounds.

A further object of the present invention is to provide pharmaceutical compositions for treating hypertension, oedema and ascites which comprise novel 1-acyl-2,3-dihydro-4(1H)-quinolinone-4-oxime-O-sulfonic acid compounds and salts thereof, solvates of said compounds and solvates of said salts as active components.

A further object of the present invention is to provide intermediate compounds, novel 1-acyl-2,3-dihydro-4(1H)-quinolinone compounds, in the synthesis of 1-acyl-2,3-dihydro-4(1H)-quinolinone-4-oxime-O-sulfonic acid compounds.

The present invention is based on the selection of 1-acyl-7-halo-2,3-dihydro-4(1H)-qinolinone-4-oxime-O-sulfonic acid compounds, namely heterocyclic- or fused heterocyclic-carbonyl derivatives at 1 position.

The compounds of the present invention containing these substituents have potent hypotensive, antioedematous and diuretic effect as well as an activity to remove ascites and are extremely useful for the treatment of diseases and disorders mentioned above.

DETAILED DESCRIPTION OF THE INVENTION

As a result of extensive investigations concerning development of novel dihydroquinolinone oxime derivatives having a satisfactory diuretic activity, the present inventors have found that 1-acyl-2,3-dihydro4(1H)-quinolinone-4-oxime-0-sulfonic acid compounds possesses a potent diuretic activity that can be used for treating and/or preventing hypertension, oedema and/or for removing ascites, thus satisfy these requirements and, have accomplished the present invention.

The present invention is directed to 1-acyl-7-halo-2,3-dihydro-4(1H)-quinolinone-4-oxime-O-sulfonic acid compounds represented by the formula (I):

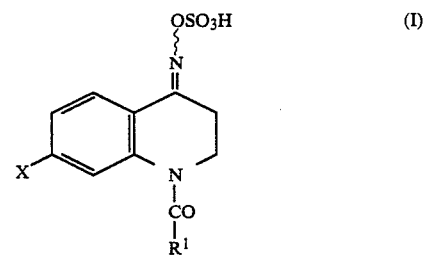

wherein $R^1$ represents a furyl group, an isoxazolyl group, a pyrrolyl group, a pyridazinyl group, a pyrimidinyl group, a quinolyl group, a benzodioxolyl group, a thienyl group, a pyridyl group, an indolyl group, an indenyl group or a phenyl group which may be substituted with at least one of an alkyl group of straight or branched chain having 1 to 4 carbon atoms, an alkylthio group, a halogen atom, an amino group, a protected amino group, a carboxyl group, an esterified carboxyl group or a phenyl group, X represents a halogen atom, and the bond shown with a wavy line represents a bond of anti-form or syn-form, and a salt thereof as well as a solvate of said compound and a solvate of said salt.

With respect to pharmaceutical uses, the compounds posessing a chlorine atom at the 7-position of the formula (I), namely 1-acyl-7-chloro-2,3-dihydro-4(1H)-quinolinone-4-oxime-O-sulfonic acids, are particularly preferred.

The present invention is also directed to a process for preparing above-mentioned 1-acyl-7-halo-2,3-dihydro-4(1H)-quinolinone-4-oxime-O-sulfonic acid compounds.

The present invention is further directed to pharmaceutical compositions for treating hypertension, oedema and removal of ascites characterized by containing these 1-acyl-7-halo-2,3-dihydro-4(1H)-quinolinone-4-oxime-O-sulfonic acid compounds and salts thereof, solvates of said compounds and solvates of said salts as active components.

The present invention is also directed to intermediate compounds, novel 1-acyl-7-halo-2,3-dihydro-4(1H)-quinolinone compounds, in the synthesis of 1-acyl-7-halo-2,3-dihydro-4(1H)-quinolinone-4-oxime-O-sulfonic acid compounds.

The compounds of the present invention represented by the formula (I) is chemically novel and can generally be produced according to the methods described below.

For example, known 7-chloro-2,3-dihydro-4(1H)-quinolinone (French Patent 1,514,280) are reacted with reactive derivatives of carboxylic acids to be introduced as the acyl moiety, preferably acid halides, in organic solvents and, if necessary and desired, in the presence of deacidifying agents to obtain 1-acyl-7-chloro-2,3-dihydro-4(1H)-quinolinone compounds as intermediate compounds.

As the organic solvent, chloroform, dichloromethane, ether, tetrahydrofuran, dioxane, benzene or ethyl acetate may be used; as the deacidifying agent, organic bases such as pyridine, triethylamine or N,N-dimethylaniline, or inorganic bases such as potassium carbonate, sodium carbonate or sodium bicarbonate may be used. As the acid halides, acid halides corresponding to $R^1$ in the formula (I), such as 2-dimethylaminobenzoyl chloride, 3-methyl-2-thienylcarbonyl chloride, 2-methyl-3-thienylcarbonyl chloride, 2-ethylthio-3-pyridylcarbonyl chloride or 1-methyl-2-pyrrolylcarbonyl chloride may be used.

The intermediate compounds thus obtained, 1-acyl-7-halo-2,3-dihydro-4(1H)-quinolinone compounds, are reacted with hydroxylamine in organic solvents such as methanol, ethanol, tetrahydrofuran or dimethylformamide to obtain corresponding 1-acyl-7-halo-2.3-dihydro-4(1H)-quinolinone-4-oximes, which are then reacted with sulfonating agents such as sulfur trioxide-pyridine complex or sulfur trioxide-dimethylformamide complex to obtain corresponding 1-acyl-7-halo-2,3-dihydro-4(1H)-quinolinone-4-oxime-O-sulfonic acid compounds, and if necessary, said compounds may form salts thereof.

The above mentioned intermediate compounds, 1-acyl-7-halo-2,3-dihydro-4(1H)-quinolinone compounds, may also be reacted with hydroxylamine-O-sulfonic acid in organic solvents such as methanol, ethanol, tetrahydrofuran or dimethylformamide in the presence of pyridine, N,N-dimethylaniline, potassium acetate, sodium carbonate or potassium carbonate to obtain 1-acyl-7-halo-2.3-dihydro-4(1H)-quinolinone-4-oxime-O-sulfonic acid compounds.

To demonstrate the utility of the compounds of the present invention, data on diuretic, antihypertensive and antioedematous activities as well as the activity to remove ascites of representative compounds are shown below.

Experimental Example 1.

Diuretic activity in dogs

Mongrel dogs weighing 7 to 15 kg were fasted overnight. The animals were restrained in a supine position under pentobarbital anesthesia (30 mg/kg body weight, i.v.), and physiological saline solution was continuously infused into femoral vein via catheter at the rate of 0.15 ml/kg/min. The animals were then laparotomized and left urethra was cannulated to collect urine in 10-minute periods. Compounds to be tested were administered intravenously and the changes in urine output was recorded. Percent increase in urine output was calculated by the formula given below:

| | | |
|---|---|---|
| Increase in urine output | = | (Urine output in the 90 minute period after the administration of the compound) − [(Urine out put in the 30-minute period before administration) × 3] |
| Percent increase in urine output | = | (Increase in urine output by the tested compound) ÷ (Increase in urine output by furosemide) × 100 |

The results are shown below:

TABLE 2

| Compound | Dose (μg/kg) | Percent increase in urine output |
|---|---|---|
| Furosemide | 100 | 100 |
| 1 | 100 | 160 |
| 3 | 100 | 191 |
| 5 | 100 | 247 |
| 7 | 100 | 217 |
| 9 | 100 | 131 |
| 13 | 100 | 221 |
| 14 | 100 | 167 |
| 15 | 100 | 176 |

All of the tested compounds showed a significant diuretic activity.

TABLE 1

| Compound No. | | | | | |
|---|---|---|---|---|---|
| | 1 | 2 | 3 | 4 | 5 |
| $R^1$ | N-methylpyrrol-2-yl | pyridin-2-yl | 3-methylpyridin-2-yl | 3-methylthiopyridin-2-yl | 3-ethylthiopyridin-2-yl |

| Compound No. | | | | | |
|---|---|---|---|---|---|
| | 6 | 7 | 8 | 9 | 10 |
| $R^1$ | pyridin-3-yl | 3-ethylthien-2-yl | 3-methyl-2-methylthien | thien-2-yl | 5-chlorothien-2-yl |

| Compound No. | | | | | |
|---|---|---|---|---|---|
| | 11 | 12 | 13 | 14 | 15 |
| $R^1$ | 3-methylthien-2-yl | furan-2-yl | 3-methylisoxazol-5-yl | 3-methylfuran-2-yl | 1,3-benzodioxol-4-yl |

Experimental Example 2.

Suppressive effect on carrageenin-induced paw oedema in rats

Compound to be tested or phenylbutazone was orally administered to groups of Wistar rats (weighing ca. 120 g), each group consisting of 3 to 5 animals. One hour after the administration, 0.1 ml of physiological saline solution containing 1% of carrageenan was subcutaneously injected to the left hind paw. The volume of each paw was measured before and 3 hours after the injection of carrageenan, and the change in the volume was divided by the volume before injection to calculate oedema index. The dose at which oedema is suppressed by 30%, $ED_{30}$, was calculated for each compound. The results are shown below.

TABLE 3

| Compound | $ED_{30}$ (mg/kg) |
| --- | --- |
| Phenylbutazone | 68 |
| 4 | 15 |
| 6 | 83 |
| 8 | 32 |

All of the tested compounds showed a significant antioedematous effect.

Experimental Example 3.

Hypotensive action in spontaneously hypertensive rats

Compound to be tested was orally administered to groups of male spontaneously hypertensive rats (SHRs, weighing 250 to 300 g), each group consisting of 3 to 5 animals, once a day for 7 consecutive days. Mean blood pressure of SHRs ranged from 170 to 190 mmHg. Blood pressure was measured before and after the administration with a plethysmograph. The results are shown below.

TABLE 4

| Compound | Dose (mg/kg) | Blood pressure Before | Blood pressure After |
| --- | --- | --- | --- |
| Control | — | 184 | 182 |
| 5 | 10 | 183 | 161 |
| 11 | 10 | 183 | 164 |
| 12 | 10 | 180 | 167 |

Significant hypotensive activity was observed for all of tested compounds.

Experimental Example 4.

Removal of ascites from tumor-bearing mice

Two days after intraperitoneal transplantation of $10^6$ cells/animal of P388 murine leukemia cells to 6-to 7-week old BDF$_1$ mice, compounds to be tested were intravenously administered to groups of the tumor-bearing mice, each group consisting of 6 animals. Five hours after the administration, the volume of ascites was measured. The ratio of removal was calculated for each compound on the relative volume of ascites. The results are shown below.

TABLE 5

| Compound | Dose (mg/kg) | Ratio of removal of ascites (%) |
| --- | --- | --- |
| Control | — | 0 |
| Furosemide | 100 | 19 |
| 2 | 10 | 38 |

TABLE 5-continued

| Compound | Dose (mg/kg) | Ratio of removal of ascites (%) |
| --- | --- | --- |
| 4 | 10 | 24 |
| 10 | 10 | 28 |

All of the compounds tested showed significant activity, more potent than furosemide, to remove ascites in tumor-bearing mice.

Experimental Example 5.

Acute toxicity

Compounds to be tested were intraperitoneally administered to groups of ICR mice weighing about 20 g. Each group consisted of 5 animals. Seven days after the administration, mortality was determined. The results are shown below.

TABLE 6

| Compound | Dose (mg/kg) | Mortality |
| --- | --- | --- |
| 1 | 200 | 0/5 |
| 5 | 200 | 0/5 |
| 7 | 200 | 0/5 |
| 8 | 200 | 0/5 |
| 10 | 200 | 0/5 |
| 13 | 200 | 0/5 |
| 14 | 200 | 0/5 |
| 15 | 200 | 0/5 |

The doses of the experiment described above are considerably higher than that required for their pharmacological activity. Therefore, these compounds were deemed to have large margins for safety.

As demonstrated by the experimental examples described above, these compounds of the present invention possess a potent diuretic activity that can be used for treating and/or preventing hypertension, oedema and/or for removing ascites, and also a large margin for safety within the dose ranges to show these pharmacological activities. Therefore, these compounds are of great use in the treatment of oedema caused by functional insufficiency of heart, kidney or liver, hypertension and accumulation of cancerous ascites.

The 1-acyl-7-halo-2,3-dihydro-4(1H)-quinolinone-4-oxime-O-sulfonic acid compounds of the present invention represented by the formula (I) may form pharmaceutically acceptable salts with organic or inorganic bases. Typical examples of such salts of the compounds represented by the formula (I) include pharmacologically acceptable salts such as alkali metal salts such as sodium salts, potassium salts, etc.; alkaline earth metal salts such as calcium salts, etc.; salts of organic bases such as ammonium salts, benzylamine salts, diethylamine salts, etc.; salts of amino acids such as arginine salts, lysine salts, etc.

The 1-acyl-7-halo-2,3-dihydro-4(1H)-quinolinone-4-oxime-O-sulfonic acid compounds provided by the present invention can be employed as pharmaceutical compositions, for example, in the form of pharmaceutical compositions containing the 1-acyl-7-halo-2,3-dihydro-4(1H)-quinolinone-4-oxime-O-sulfonic acid compounds together with appropriate, pharmaceutically acceptable carriers. The pharmaceutical composition may take a solid form, for example, tablets, granules, subtilized granules, powders, capsules and suppositories or a liquid form, for example, aqueous solutions for injection or suspensions for injection prepared with suspending excipients such as Tween 80 or arabic gum. The compositions may be administered orally or intravenously, but can also be administered subcutaneously, intradermally or intramuscularly. Further, the composition may be formulated for the administration by inhalation, for example as aerosol, for topical application as ointment, or as suppositories. While dose varies depending upon age and conditions of the patient, conditions and kind of diseases, etc., from about 1 to about 5000 mg, preferably from about 10 to about 1000 mg, can be used as a daily dose for an adult.

Hereafter the present invention will be described with reference to the examples below but is not deemed to be limited thereof.

Example 1

Preparation of 7-chloro-2,3-dihydro-1-(2-dimethylaminobenzoyl)-4(1H)-quinolinone To a mixture of 7-chloro-2,3-dihydro-4(1H)-quinolinone (20 g), pyridine (26 g) and dioxane (200 ml) was added dropwise 2-dimethylaminobenzoyl chloride (30 g) under cooling at 0° C. to 5° C. with stirring. The mixture was allowed to react at room temperature for additional 3 hours. The reaction mixture was poured into 500 ml of water, then shaken with additional dichloromethane (1000 ml). The organic layer was washed once with 1 N HCl (100 ml), twice with water (200 ml each) then once with saturated aqueous NaCl solution and dried over anhydrous sodium sulfate. Dichloromethane was removed in vacuo and the residue was recrystallized with dichloromethane and n-hexane to obtain 7-chloro-2,3-dihydro-1-(2-dimethylaminobenzoyl)-4(1H)-quinolinone (yield 35 g) as white crystal.

Melting point: 85.5–89.0° C.
IR (KBr, cm$^{-1}$): 1690, 1650, 1435, 1375
NMR (CDCl$_3$, ppm): 2.51 (6H, s), 2.78 (2H, t), 4.34 (2H, t), 6.88–7.93 (7H, m).

Example 2

Preparation of 7-chloro-2,3-dihydro-1-(2-dimethylaminobenzoyl)-4(1H)-quinolinone-4-oxime-O-sulfonic acid potassium salt.

To a mixture of 7-chloro-2,3-dihydro-1-(2-dimethylaminobenzoyl)-4(1H)-quinolinone (14.5 g), obtained in example 1, methanol (200 ml) and dichloromethane (200 ml) was added 6.1 g of hydroxylamine-O-sulfonic acid with stirring at room temperature. After stirring for 30 minutes at room temperature, aqueous solution of potassium carbonate (7.3 g in 10 ml of water) was added to the mixture at once and stirring was continued for another 2 hours. Precipitated crystals were removed by filtration and the solvent was removed in vacuo. The residue was subjected to silica gel column chromatography using a dichloromethane-methanol mixture (10 1), then recrystallized with a mixed solvent of methanol and carbon tetrachloride to obtain 7-chloro-2,3-dihydro1-(2-dimethylaminobenzoyl)-4(1H)-quinolinone-4-oxime O-sulfonic acid potassium salt (yield 10.0 g) as white crystal.

Melting point: 182° C. (decomposition)
IR (KBr, cm$^{-1}$): 1655, 1380, 1240.
NMR (DMSO-d$_6$, ppm): 2.44 (6H, s), 2.83 (2H, t), 4.24 (2H, t), 6.80–7.93 (7H, m)

Example 3

Preparation of 7-chloro-1-(2-ethylthio-3-pyridylcarbonyl)-2.3-dihydro-4(1H)-quinolinone.

To a mixture of 7-chloro-2,3-dihydro-4(1H)-quinolinone (25 g), pyridine (32 g) and dioxane (200 ml) was added dropwise 2-ethylthio-3-pyridylcarbonyl chloride (37 g) under cooling at 0 C. to 5° C. with stirring. The mixture was allowed to react at room temperature for additional 3 hours. The reaction mixture was subjected to the procedure described in example 1, and 43 g of 7-chloro-1-(2-ethylthio-3-pyridylcarbonyl)-2,3-dihydro-4(1H)-quinolinone was obtained as white crystal.

Melting point: 120.0–122.8° C.
IR (KBr, cm$^{-1}$): 1700, 1640, 1400, 1370
NMR (CDCl$_3$, ppm): 1.16 (3H, t), 2.87 (2H, t), 3.13 (2H, q), 4.13 (2H, t), 7.12–8.57 (6H, m)

Example 4

Preparation of 7-chloro-1-(2-ethylthio-3-pyridylcarbonyl)-2,3-dihydro-4(1H)-quinolinone-4-oxime-O-sulfonic acid potassium salt (Compound 5)

To a mixture of 7-chloro-1-(2-ethylthio-3-pyridylcarbonyl)-2,3-dihydro-4(1H)-quinolinone (10.0 obtained in example 3, methanol (150 ml) and dichloromethane (100 ml) was added hydroxylamine-O-sulfonic acid (4 at room temperature with stirring. The mixture was stirred at room temperature for 30 minutes, and aqueous solution of potassium carbonate.(4.8 g in 20 ml of water) was added at once. The reaction mixture was stirred at room temperature for 2 hours, and the solvent was removed in vacuo. The residue was subjected to silica gel çolumn chromatography using dichloromethanemethanol mixture (5 : 1) to obtain 7-chloro-1-(2-ethylthio-3-pyridylcarbonyl)-2,3-dihydro-4(1H)-quinolinone-4-oxime-O-sulfonic acid potassium salt (yield 10.0 g) as white crystal.

Melting point: 162.0° C. (decomposition)
IR (KBr, cm$^{-1}$): 1655, 1390, 1250
NMR (DMSO-d$_6$, ppm): 1.18 (3H, t), 2.90 (2H, t), 3.13 (2H, q), 3.80 (2H, t), 7.10–8.55 (6H, m).

Example 5

Preparation of 7-chloro-2,3-dihydro-1-(2-methyl-3-thienylcarbonyl)-4(1H)-quinolinone To a mixture of 7-chloro-2,3-dihydro-4(1H)-quinolinone (20.0 g), pyridine (26 g) and dichloromethane (200 ml) was added dropwise 2-methyl-3-thienylcarbonyl chloride (26 g) at room temperature with stirring. The mixture was stirred under reflux for 4 hours. The reaction mixture was poured into 500 ml of water, then shaken with additional dichloromethane (1000 ml). The organic layer was washed once with 1 N HCl (100 ml), twice with water (200 ml each) and once with saturated aqueous NaCl solution, then dried over anhydrous sodium sulfate. Solvent was removed in vacuo and 7-chloro-2,3-dihydro-1-(2-methyl-3-thienylcarbonyl)-4(1H)-quinolinone (yield 28 g) was obtained as colorless oil.

IR (KBr, cm$^{-1}$): 1690, 1650, 1590, 1365
NMR (DMSO-d$_6$, ppm): 2.41 (3H, s), 2.84 (2H, t), 4.16 (2H, t), 7.01 (1H, d), 7.25–7.38 (3H, m), 7.88 (1H, d).

Example 6

Preparation of 7-chloro-2,3-dihydro-1-(2-methyl-3-thienylcarbonyl)-4(1H)-quinolinone-4-oxime-O-sulfonic acid potassium salt (compound 11).

(Step 1)

To a mixture of 7-chloro-2,3-dihydro-1-(2-methyl-3-thienylcarbonyl)-4(1H)-quinolinone (17.5 g), obtained in example 5, and ethanol (250 ml) were added hydroxyl amine hydrochloride (8 g) and pyridine (8.8 g), and the mixture was heated under reflux for 1.5 hours. After cooling, the reaction mixture was poured into 1000 ml of water, and precipitated crystals were separated by filtration, washed, dried and recrystallized with ethanol to obtain 7-chloro-2,3-dihydro-1-(2-methyl-3-thienylcarbonyl)-4(1H)-quinolinone-4-oxime (yield 16 g) as white crystal.

Melting point: 143.1° C. (decomposition)

IR (KBr, cm$^{-1}$): 3300, 1610, 1485, 1390

NMR (DMSO-d$_6$, ppm): 2.29 (3H, s), 2.85 (2H, t), 3.87 (2H, t), 6.92 (1H, d), 7.00 (1H, d), 7.18 (1H, dd), 7.32 (1H, d), 7.87 (1H, d), 11.55 (1H, s).

(Step 2)

The product of Step 1 (16 g) was dissolved in dichloromethane (250 ml) and sulfur trioxide-pyridine complex (8 g) was added. The reaction mixture was stirred at room temperature for 24 hours and the solvent was removed in vacuo. To the residue was added methanol (200 ml) and then aqueous potassium carbonate solution (9 g in 10 ml of water) at once, and the mixture was subjected to the procedure described in example 4, and 13 g of 7-chloro-2,3-dihydro-1-(2-methyl-3-thienylcarbonyl)-4(1H) quinolinone-4-oxime-O-sulfonic acid potassium salt was obtained as white crystal.

Melting point: 167.7° C. (decomposition)

IR (KBr, cm$^{-1}$): 1660, 1390, 1280, 1250

NMR (DMSO-d$^6$, ppm): 2.31 (3H, s), 2.85 (2H, t), 3.87 (2H, t), 6.93 (1H, d), 7.02 (1H, d), 7.23 (1H, dd), 7.32 (1H, d), 7.93 (1H, d).

Example 7

Preparation of 7-chloro-2,3-dihydro-1-(1-methyl-2-pyrrolylcarbonyl)-4(1H)-quinolinone.

To a mixture of 7-chloro-2,3-dihydro-4(1H)-quinolinone (15 g), pyridine (12 g) and dichloromethane (200 ml) was added dropwise 1-methyl-2-pyrrolyl chloride (17 g) under cooling at 0° C. to 5° C. with stirring. The mixture was subjected to the procedure described in example 1, and 21 g of 7-chloro-2,3-dihydro-1-(1-methyl-2-pyrrolylcarbonyl)-4(1H)-was obtained as white crystal.

Melting point: 131.2–132.2° C.

IR (KBr, cm$^{-1}$): 1695, 1620, 1590, 1410, 1385

NMR (CDCl$_3$, ppm): 2.82 (2H, t), 3.90 (3H, s), 4.38 (2H, t), 6.06 (1H,dd), 6.35 (1H,dd), 6.80 (1H, m), 7.12 (1H,dd), 7.28 (1H,dd), 7.96 (1H, d).

Example 8

Preparation of 7-chloro-2,3-dihydro-1-(1-methyl-2-pyrrolylcarbonyl)-4(1H)-quinolinone-4-oxime-O-sulfonic acid sodium salt.

To a mixture of 7-chloro-2,3-dihydro-1-(1-methyl-2-pyrrolylcarbonyl)-4(1H)-quinolinone (14.5 g), obtained in example 7, methanol (200 ml) and dichloromethane (200 ml was added 6.8 of hydroxylamine-0-sulfonic acid with stirring at room temperature After stirring for 30 minutes at room temperature, aqueous solution of sodium carbonate (6.4 g in 10 ml of water) was added to the mixture at once and stirring was continued for another 2 hours. Precipitated crystals were removed by filtration and the solvent was removed in vacuo. The residue was subjected to silica gel column chromatography using a dichloromethane-methanol mixture (10 1) to obtain 7-chloro-2,3-dihydro-1-(1-methyl-2-pyrrolylcarbonyl)-4(1H)-quinolinone-4-oxime-O-sulfonic acid sodium salt (yield 12.0 g) as white crystal.

Melting point: 176.5° C. (decomposition)

IR (KBr, cm$^{-1}$): 1645, 1410, 1380, 1250

NMR (DMSO-d$_6$, ppm): 2.85 (2H, t), 3.78 (3H, s), 3.98 (2H, t), 6.00 (1H,dd), 6.20 (1H,dd), 6.95 (1H, m), 7.06–7.24 (2H, m) 7.95 (1H, d).

Compounds of examples 9 to 69 are summarized to the following Tables 8 to 9 together with corresponding IR and NMR data (NMR data were generally measured at 90 MHz except several data, which were measured at 60 MHz and marked with asterisks(*), and NMR data were generally measured in DMSO-d$^6$ except several data, which were measured in CDCl$_3$ and marked with dagger ( † )), and melting or decomposition points. The methods by which these compounds are synthesized can be classified into three groups as shown below.

TABLE 7

| Group | Synthetic method (representative example number) | Example number in Tables 8 to 9 |
| --- | --- | --- |
| A | 1, 3, 5, 7 | 40–69 |
| B | 2, 4 | 9–39 |
| C | 6 | 32–34 |

TABLE 8

Structure: 7-chloro-3,4-dihydroquinoline with =N-OSO₃K at position 4 and N-CO-R¹ at position 1

| Exp. No. | Comp. No. | R¹ | IR(KBr, cm⁻¹) | NMR(DMSO-d₆, ppm) | Decomp. (°C.) |
|---|---|---|---|---|---|
| 9 | | pyridazinyl (N–N) | 1655, 1400, 1275, 1240 | 2.92(2H, t), 3.92(2H, t), 7.20–7.36(2H, m), 7.80–8.15(3H, m), 9.30(1H, m) | 202.7 |
| 10 | | pyrimidinyl | 1675, 1580, 1420, 1280, 1250 | 2.88(2H, t), 3.85(2H, t), 7.22–7.34(2H, m), 7.80–7.99(2H, m), 8.96–9.19(2H, m) | 209.5 |
| 11 | | 5-methylthiophen-2-yl (CH₃ on S ring) | 1630, 1605, 1450, 1240 | 2.45(3H, s), 2.85(2H, t), 3.96(2H, t), 6.75(1H, d), 7.02–7.30(3H, m), 7.90(1H, d) | 165.5 |
| 12 | 8 | 3-methylthiophen-2-yl (H₃C) | 1640, 1415, 1245 | 2.04(3H, s), 2.87(2H, t), 3.93(2H, t), 6.85–8.02 (5H, m) | 103.0 |
| 13 | | 3,4-dimethylthiophen-2-yl | 1655, 1485, 1280, 1235 | 2.11(3H, s), 2.84(2H, t), 3.86(2H, t), 7.11(1H, d), 7.17–7.29(2H, m), 7.68(1H, d), 7.94(1H, d) | 171.3 |
| 14 | 10 | 5-chloro-3-methylthiophen-2-yl | 1640, 1485, 1420, 1245 | 2.86(2H, t), 3.89(2H, t), 7.12(1H, d), 7.20(1H, d), 7.26(1H, dd), 7.56(1H, d), 7.94(1H, d) | 186.5 |
| 15 | | 5-methylthio-3-methylthiophen-2-yl (H₃CS) | 1640, 1410, 1270, 1240 | 2.31(3H, s), 2.86(2H, t), 3.88(2H, t), 7.01(1H, d), 7.13(1H, d), 7.24(1H, dd), 7.62(1H, d), 7.94(1H, d) | 183.2 |
| 16 | 7 | 5-ethyl-3-methylthiophen-2-yl (H₅C₂) | 1645, 1480, 1375, 1240 | 1.14(3H, t), 2.75(2H, q), 2.84(2H, t), 3.86(2H, t), 6.93(1H, d), 7.12(1H, dd), 7.28(1H, d), 7.36(1H, d), 7.94(1H, d) | 163.4 |
| 17 | | furan-2-yl | 1640, 1480, 1390, 1250 | 2.84(2H, t), 3.95(2H, t), 6.60(1H, dd), 6.95–7.10 (2H, m), 7.22(1H, dd), 7.78(1H, d), 7.92(1H, d) | 146.4 |
| 18 | 12 | 3-methylfuran-2-yl | 1640, 1610, 1480, 1390, 1250 | 2.84(2H, t), 3.92(2H, t), 6.46(1H, d), 7.15–7.35 (2H, m), 7.68(1H, m), 7.92(1H, d), 8.04(1H, s) | 155.9 |

TABLE 8-continued

[Structure: 7-chloro-2,3-dihydroquinoline with =N-OSO₃K at 4-position and N-CO-R¹ at 1-position]

| Exp. No. | Comp. No. | R¹ | IR(KBr, cm⁻¹) | NMR(DMSO-d₆, ppm) | Decomp. (°C.) |
|---|---|---|---|---|---|
| 19 | 1 | 1-methylpyrrol-2-yl (N-CH₃) | 1645, 1410, 1380, 1250 | 2.82(2H, t), 3.78(3H, s), 3.96(2H, t), 6.00(1H, dd) 6.20(1H, dd), 6.95(1H, m), 7.06–7.24(2H, m), 7.95(1H, d) | 172.8 |
| 20 | | 3-bromo-5-methylpyridin-yl | 1650, 1410, 1380, 1245 | 2.88(2H, t), 3.84(2H, t), 7.18–7.34(2H, m), 7.98(1H, d), 8.20(1H, s), 8.60(1H, d), 8.80(1H, d) | 167.6 |
| 21 | 3 | 2-methyl-3-(methylthio?)... 2-methylthio-3-methylpyridine | 1660, 1480, 1380, 1280, 1240 | 2.50(3H, s), 2.84(2H, t), 3.76(2H, t), 7.15–7.65(3H, m), 7.84–8.05(2H, m), 8.56(1H, dd) | 210.8 |
| 22 | 4 | 2-(methylthio)-3-methylpyridin-yl (H₃CS, N) | 1660, 1390, 1240 | 2.48(3H, s), 2.89(2H, t), 3.79(2H, t), 7.10–8.57(6H, m)* | 191.0 |
| 23 | | 2-(pentylthio)-3-methylpyridin-yl (H₁₁C₅S, N) | 1660, 1390, 1240 | 0.84(3H, t), 1.36(6H, m), 2.89(2H, t), 3.13(2H, t), 3.81(2H, t), 7.21–8.54(6H, m)* | 162.0 |
| 24 | 13 | 3,4,5-trimethylisoxazol-yl | 1660, 1420, 1245 | 2.10(3H, s), 2.24(3H, s), 2.88(2H, t), 3.91(2H, t), 7.21–8.05(3H, m)* | 169.0 |
| 25 | | 2,3-dimethylindenyl | 1645, 1380, 1260, 1240 | 1.96(3H, s), 2.88(2H, t), 3.70(2H, s), 3.93(2H, t), 7.20(1H, d), 7.20–7.55(5H, m), 7.96(1H, d) | 203.8 |
| 26 | | 4-methylquinolin-yl | 1655, 1400, 1380, 1245 | 2.92(2H, t), 3.65(2H, t), 7.33(1H, d), 7.70–8.16(7H, m), 8.99(1H, d) | 222.8 |
| 27 | | 1,2-dimethylindol-yl | 1640, 1480, 1400, 1240 | 2.89(2H, t), 3.86(3H, s), 4.02(2H, t), 6.65(1H, s), 7.08–7.62(6H, m), 7.97(1H, d) | 176.6 |
| 28 | 14 | 2,4-dimethyl-3-methyl-furyl | 1654, 1648, 1613, 1558, 1484, 1406, 1276, 1250 | 1.81(3H, s), 2.09(3H, s), 2.85(2H, t), 3.90(2H, t), 7.06(1H, d), 7.26(1H, dd), 7.35(1H, s), 7.94(1H, d) | 152.9 |

TABLE 8-continued

[Structure: 7-chloro-3,4-dihydroquinoline with =N-OSO₃K at position 4 and N-CO-R¹ at position 1]

| Exp. No. | Comp. No. | R¹ | IR(KBr, cm⁻¹) | NMR(DMSO-d₆, ppm) | Decomp. (°C.) |
|---|---|---|---|---|---|
| 29 | 15 | 4-methyl-1,3-benzodioxole | 1654, 1457, 1380, 1244, 1066 | 2.82(2H, t), 3.89(2H, t), 5.84(2H, s), 6.94–7.37(5H, m), 7.96(1H, d) | 117.4 |
| 30 | | 3-methyl-4-methylpyridine (4-CH₃, 3-yl pyridine) | 1656, 1393, 1270, 1235, 1068 | 2.25(3H, s), 2.87(2H, t), 3.30(2H, t), 7.08–7.38(3H, m), 7.97(1H, d), 8.34–8.58(2H, m) | 222.8 |
| 31 | | 4-C₄H₉-pyridin-3-yl | 1655, 1396, 1273, 1245, 1067 | 0.86(3H, t), 1.20–1.70(4H, m), 2.60(2H, t), 2.84(2H, t), 3.78(2H, t), 7.20–7.40(3H, m), 7.97(1H, d), 8.40–8.60(2H, m) | 178.0 |
| 32 | | 1-methyl-pyrrol-3-yl | 1652, 1590, 1536, 1400, 1258 | 2.77(2H, t), 3.62(3H, s), 3.95(2H, t), 6.04(1H, dd), 6.70(1H, t), 7.13–7.24(3H, m), 7.91(1H, d) | 165.2 |
| 33 | | 2-isopropyl-3-methyl-pyridin-? | 1661, 1395, 1272, 1247, 1120, 1067 | 1.20(6H, d), 2.85(2H, t), 3.05(1H, m), 3.75(2H, t), 7.25–7.36(3H, m), 7.76–8.02(2H, m), 8.62(1H, dd) | 198.8 |
| 34 | | 4-SC₂H₅-pyridin-3-yl | 1655, 1630, 1410, 1239, 1064 | 1.22(3H, t), 2.89(2H, t), 3.06(2H, q), 3.81(2H, t), 7.21(1H, s), 7.23(1H, d), 7.41(1H, d), 7.96(1H, d), 8.46(1H, d), 8.46(1H, s) | 171.2 |
| 35 | 2 | pyridin-3-yl | 1665, 1395, 1215 | 2.93(2H, t), 3.90(2H, t), 7.20–7.62(3H, m), 7.95–8.06(2H, m), 8.70–8.77(2H, m) | 208.9 |
| 36 | 6 | pyridin-4-yl | 1640, 1405, 1225 | 2.91(2H, t), 3.80(2H, t), 7.24–7.53(2H, m), 7.90–8.09(3H, m), 8.88–8.98(2H, m) | 242.0 |
| 37 | 9 | thien-3-yl | 1640, 1405, 1240 | 2.87(2H, t), 3.93(2H, t), 7.09–8.02(6H, m) | 155.8 |

TABLE 8-continued

[Structure: 7-chloro-3,4-dihydroquinolin-4-one oxime O-sulfate potassium salt with N-CO-R¹ substituent]

| Exp. No. | Comp. No. | R¹ | IR(KBr, cm⁻¹) | NMR(DMSO-d₆, ppm) | Decomp. (°C.) |
|---|---|---|---|---|---|
| 38 | | 2-(CO₂CH₃)-phenyl | 1725, 1665, 1390, 1240 | 2.84(2H, t), 3.74(5H, m), 7.17–8.02(7H, m)* | 156 |
| 39 | | 2-(C₆H₅)-phenyl | 1650, 1380, 1240 | 2.8(2H, t), 4.0(2H, t), 7.0–7.7(12H, m)* | 150.5 |

NMR data marked with asterisks(*) were measured at 60 MHz.

TABLE 9

[Structure: 7-chloro-2,3-dihydroquinolin-4(1H)-one with N-CO-R¹ substituent]

| Exp. No. | R¹ | IR(KBr, cm⁻¹) | NMR(DMSO-d₆, ppm) | M. P. (°C.) |
|---|---|---|---|---|
| 40 | pyridazin-3-yl (N—N) | 1695, 1660, 1590, 1380 | 2.88(2H, t), 4.22(2H, t), 7.28–7.55(2H, m), 7.80–8.20(3H, m), 9.30(1H, m) | 174.7–176.3 |
| 41 | pyrimidin-4-yl (N, N) | 1690, 1655, 1590, 1370 | 2.86(2H, t), 4.18(2H, t), 7.32–7.67(2H, m), 7.85–7.99(2H, m), 9.04–9.26(2H, m), | 148.2–151.3 |
| 42 | 2,5-dimethylthiophen-3-yl | 1690, 1630, 1595, 1460, 1365 | 2.52(3H, s), 2.82(2H, t), 4.34(2H, t), 6.65(1H, d), 7.05–7.30(3H, m), 7.92(1H, d) | 131.2–133.4 † |
| 43 | 2,3-dimethylthiophen-? (H₃C, CH₃ on thiophene) | 1695, 1640, 1470, 1420, 1360 | 2.11(3H, s), 2.85(2H, t), 4.22(2H, t), 6.90–7.96(5H, m)* | 93.0–99.5 |
| 44 | 3-methylthiophen-2-yl (CH₃) | 1690, 1650, 1590, 1440 | 2.23(3H, s), 2.82(2H, t), 4.28(2H, t), 6.98–7.03(1H, m), 7.15(1H, d), 7.16(1H, dd), 7.40(1H, d), 7.98(1H, d) | oil † |

TABLE 9-continued

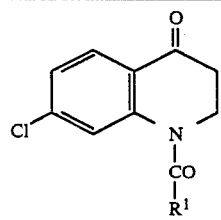

| Exp. No. | R¹ | IR(KBr, cm⁻¹) | NMR(DMSO-d₆, ppm) | M.P. (°C.) |
|---|---|---|---|---|
| 45 | 3-methyl-2-chlorothiophene | 1690, 1645, 1590, 1460 | 2.85(2H, t), 4.20(2H, t), 7.22(1H, d), 7.28(1H, d), 7.33(1H, dd), 7.58(1H, d), 7.88(1H, d) | 109.1~110.8 |
| 46 | 3-methyl-2-(methylthio)thiophene | 1690, 1650, 1595, 1400 | 2.36(3H, s), 2.83(2H, t), 4.19(2H, t), 7.15-7.20(2H, m), 7.30(1H, dd), 7.64(1H, d), 7.87(1H, d) | oil |
| 47 | 3-methyl-2-ethylthiophene | 1690, 1660, 1585, 1460 | 1.28(3H, t), 2.84(2H, q), 2.95(2H, t), 4.27(2H, t), 6.83(1H, d), 7.07-7.21(3H, m), 7.95(1H, d) | oil † |
| 48 | 2-methylfuran | 1690, 1640, 1580, 1560, 1470 | 2.82(2H, t), 4.30(2H, t), 6.50(1H, dd), 7.02-7.28(3H, m), 7.42(1H, d), 7.90(1H, d) | 132.0~134.2 † |
| 49 | 3-methylfuran | 1695, 1650, 1595, 1480, 1400 | 2.82(2H, t), 4.30(2H, t), 6.30(1H, d), 7.10-7.45(3H, m), 7.80(1H, s), 7.95(1H, d) | 151.3~152.7 † |
| 50 | 3-bromo-5-methylpyridine | 1680, 1655, 1590, 1365 | 2.88(2H, t), 4.30(2H, t), 7.15(1H, d), 7.25(1H, dd), 7.95-8.10(2H, m), 8.60(1H, d), 8.82(1H, d) | 166.5~168.9 † |
| 51 | 2,3-dimethylpyridine | 1685, 1635, 1580, 1465, 1365 | 2.46(3H, s), 2.80(2H, t), 4.02(2H, t), 7.15-7.40(2H, m), 7.55(1H, m), 7.75-7.94(2H, m), 8.50(1H, dd) | 102.5~106.4 |
| 52 | 3-methyl-2-(methylthio)pyridine | 1700, 1650, 1560, 1400, 1360 | 2.49(3H, s), 2.85(2H, t), 4.10(2H, t), 7.12-8.58(6H, m)* | 170.0~171.0 |
| 53 | 3-methyl-2-(pentylthio)pyridine | 1700, 1655, 1400, 1370 | 0.84(3H, t), 1.33(6H, m), 2.87(2H, t), 3.11(2H, t), 4.14(2H, t), 7.11-8.56(6H, m)* | 90.5~92.0 |
| 54 | 3,5-dimethylisoxazole | 1700, 1655, 1420, 1370 | 2.15(3H, s), 2.31(3H, s), 2.85(2H, t), 4.20(2H, t), 7.25-7.98(3H, m)* | 146.0~148.0 |

TABLE 9-continued
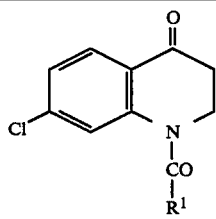
| Exp. No. | R¹ | IR(KBr, cm⁻¹) | NMR(DMSO-$d_6$, ppm) | M. P. (°C.) |
|---|---|---|---|---|
| 55 | 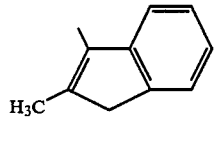 | 1685, 1640, 1590, 1370 | 2.04(3H, s), 2.87(2H, t), 3.75(2H, s), 4.22(2H, t), 7.20–7.60(6H, m), 7.90(1H, d) | 114.0~118.7 |
| 56 | 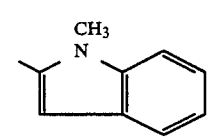 | 1695, 1645, 1590, 1370 | 2.82(2H, t), 3.95(2H, t), 7.41(1H, dd), 7.67–8.18(7H, m), 9.02(1H, d) | 167.9~170.2 |
| 57 | 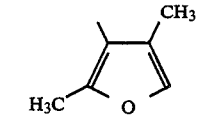 | 1695, 1645, 1590, 1465 | 2.88(2H, t), 3.89(3H, s), 4.27(2H, t), 6.81(1H, s), 7.02–7.65(6H, m), 7.91(1H, d) | 73.1~77.5 |
| 58 | 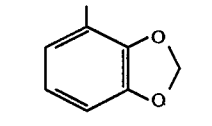 | 1697, 1654, 1595, 1401 | 1.87(3H, d), 2.21(3H, s), 2.80(2H, t), 4.29(2H, t), 7.08–7.26(3H, m), 7.95(1H, d) | oil † |
| 59 | 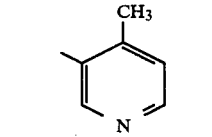 | 1687, 1651, 1597, 1565, 1472, 1458, 1368, 1355, 1205 | 2.84(2H, t), 4.30(2H, t), 5.70(2H, s), 6.90–7.26(5H, m), 7.95(1H, d) | 195.5~196.5 † |
| 60 | 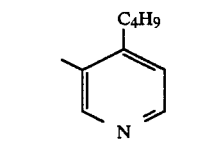 | 1697, 1655, 1594, 1375 | 2.38(3H, s), 2.82(2H, t), 4.20(2H, t), 7.05–7.32(3H, m), 7.98(1H, d), 8.28–8.58(2H, m) | oil † |
| 61 | 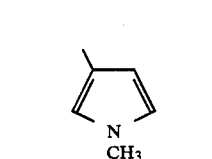 | 1698, 1662, 1593, 1374 | 0.93(3H, t), 1.20–1.90(4H, m), 2.50–3.00(4H, m), 4.17(2H, t), 7.20–7.60(3H, m), 7.99(1H, d), 8.51(1H, d), 8.60(1H, s) | oil † |
| 62 | 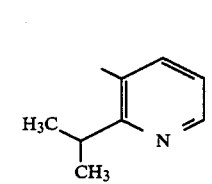 | 1689, 1634, 1595, 1208 | 2.79(2H, t), 3.67(3H, s), 4.32(2H, t), 6.10(1H, dd), 6.50(1H, t), 7.03–7.15(2H, m), 7.34(1H, d), 7.92(1H, d) | 128.4~131.5 † |
| 63 |  | 1696, 1654, 1593, 1381 | 1.27(6H, d), 2.79(2H, t), 3.14(1H, m), 4.14(2H, t), 7.11–7.27(2H, m), 7.47–7.58(2H, m), 7.99(1H, d), 8.69(1H, dd) | 150.6~153.2 † |

TABLE 9-continued

[Structure: 7-chloro-2,3-dihydroquinolin-4(1H)-one with N-CO-R¹ substituent]

| Exp. No. | R¹ | IR(KBr, cm⁻¹) | NMR(DMSO-d₆, ppm) | M. P. (°C.) |
|---|---|---|---|---|
| 64 | 3-methyl-4-(SC₂H₅)-pyridyl | 1697, 1654, 1595, 1570, 1467, 1375, 1208 | 1.20(3H, t), 2.87(2H, t), 3.07(2H, q), 4.12(2H, t), 7.33(1H, d), 7.34(1H, s), 7.40(1H, d), 7.88(1H, d), 8.47(1H, d), 8.51(1H, s) | oil |
| 65 | 5-methyl-3-pyridyl | 1690, 1635, 1470, 1360 | [DMSO-d₆/CDCl₃] 2.90(2H, t), 4.21(2H, t), 7.26–7.58(3H, m), 7.90–8.09(2H, m), 8.70–8.86(2H, m) | 175.8~177.8 |
| 66 | 3-methyl-4-pyridyl | 1685, 1640, 1490, 1400 | 2.93(2H, t), 4.10(2H, t), 7.35–8.01(2H, m), 8.07–8.25(2H, m) 8.60–8.82(1H, m), 8.94–9.02(2H, m) | 171.7~179.2 |
| 67 | 3-methyl-2-thienyl | 1660, 1640, 1475, 1345 | 2.86(2H, t), 4.32(2H, t), 7.11–8.02(6H, m) | 165.1~166.9 |
| 68 | 2-(CO₂CH₃)-phenyl | 1725, 1700, 1675, 1375 | 2.81(2H, t), 4.01(5H, m), 7.22–7.96(7H, m)* | 129~130.5 |
| 69 | 2-(C₆H₅)-phenyl | 1695, 1650, 1365 | 2.1(2H, t), 3.4(2H, t), 6.8–7.8(12H, m)* | 129.5~131.5 |

NMR data marked with asterisks (*) were measured at 60 MHz.
NMR data marked with dagger (†) were measured in CDCl₃.

Now, typical but non-limiting examples of formulations of the compound of this invention will be shown below.

Formulation 1 (Capsules)

Compound 13, 40 g of weight, 645 g of lactose and 15 g of magnesium stearate were weighed and mixed until the mixture became homogeneous The mixture was then filled in No. 1 hard gelatin capsule at 350 mg each to obtain capsule preparation.

Formulation 2 (Tablets)

Compound 7, 50 g of weight, 800 g of lactose. 120 g of potato starch, 15 g of polyvinyl alcohol and 15 g of magnesium stearate were weighed. The weighed amount of compound 7, lactose and potato starch were mixed until accomplishing homogeneity. Then aqueous solution of polyvinylalcohol was added to the mixture and granulated by wet process. The granules were then dried, mixed with magnesium stearate and pressed into tablets, each weighing 200 mg.

Formulation 3 (Powder)

Compound 15, 100 g of weight, 890 g of lactose and 10 g of magnesium stearate were weighted and mixed until the mixture became homogeneous to obtain 10% powder preparation.

Formulation 4 (Rectal suppository)

Compound 3, 100 g of weight, 180 g of polyethyleneglycol 1500, 720 of polyethyleneglycol 4000 were ground well in a mortar and formulated into suppository by melting and casting in appropriate mold.

Formulation 5 (Injection)

Compound 5, 1 of weight, was weighed and dissolved in 200 ml of distilled water for injection. The solution was filtered, sterilized. Two milliliters each of the sterilized solution was poured into 5-ml ampoules and sealed to obtain preparation for injection.

What is claimed is:

1. A 1-acyl-7-halo-2,3-dihydro-4(1H)-quinolinone-4-oxime-O-sulfonic acid compound represented by the formula (I):

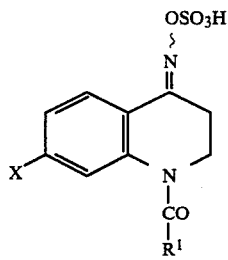

wherein R¹ represents a phenyl group substituted with at least one of an alkylthio group, an amino group which may be substituted with one or two alkyl groups of straight or branched chain having 1 to 4 carbon atoms, a carboxyl group, an alkyloxycarbonyl group of straight or branched chain having 1 to 4 carbon atoms or a phenyl group, or wherein R¹ represents a furyl group, an isoxazolyl group, a pyrrolyl group, a pyridazinyl group, a pyrimidinyl group, a quinolyl group, a benzodioxolyl group, a thienyl group, a pyridyl group, an indolyl group or an indenyl group any one of which may be substituted with at least one of an alkyl group of straight or branched chain having 1 to 4 carbon atoms, an alkylthio group, a halogen atom, an amino group which may be substituted with one or two alkyl groups of straight or branched chain having 1 to 4 carbon atoms, a carboxyl group, an alkyloxycarbonyl group of straight or branched chain having 1 to 4 carbon atoms or a phenyl group, provided that when R¹ represents a thienyl group or a pyridyl group, either group is substituted with at least one of said substituents, X represents a halogen atom, and the bond shown with a wavy line represents a bond of anti-form or syn-form, and a salt thereof as well as a solvate of said compound and a solvate of said salt.

2. A 1-acyl-7-halo-2,3-dihydro-4(1H)-quinolinone-4-oxime-O-sulfonic acid compound as claimed in claim 1 wherein R¹ represents a N-methylpyrrol-2-yl group.

3. A 1-acyl-7-halo-2,3-dihydro-4(1H)-quinolinone-4-oxime-O-sulfonic acid compound as claimed in claim 1 wherein R¹ represents furyl group.

4. A 1-acyl-7-halo-2,3-dihydro-4(1H)-quinolinone-4-oxime-O-sulfonic acid compound as claimed in claim 1 wherein R¹ represents a 2,4-dimethylfuran-3-yl group.

5. A 1-acyl-7-halo-2,3-dihydro-4(1H)-quinolinone-4-oxime-O-sulfonic acid compound as claimed in claim 1 wherein R¹ represents a 2-methylthiophen-3-yl group.

6. A 1-acyl-7-halo-2,3-dihydro-4(1H)-quinolinone-4-oxime-O-sulfonic acid compound as claimed in claim 1 wherein R¹ represents a 3-methylthiophen-2-yl group.

7. A 1-acyl-7-halo-2,3-dihydro-4(1H)-quinolinone-4-oxime-O-sulfonic acid compound as claimed in claim 1 wherein R¹ represents a 4-methylthiophen-3-yl group.

8. A 1-acyl-7-halo-2,3-dihydro-4(1H)-quinolinone-4-oxime-O-sulfonic acid compound as claimed in claim 1 wherein R¹ represents a 2-ethylthiophen-3-yl group.

9. A 1-acyl-7-halo-2,3-dihydro-4(1H)-quinolinone-4-oxime-O-sulfonic acid compound as claimed in claim 1 wherein R¹ represents a 2-chlorothiophen-3-yl group.

10. A 1-acyl-7-halo-2,3-dihydro-4(1H)-quinolinone-4-oxime-O-sulfonic acid compound as claimed in claim 1 wherein R¹ represents a 2-methylpyridin-3-yl group.

11. A 1-acyl-7-halo-2,3-dihydro-4(1H)-quinolinone-4-oxime-O-sulfonic acid compound as claimed in claim 1 wherein R¹ represents a 4-methylpyridin-3-yl group.

12. A 1-acyl-7-halo-2,3-dihydro-4(1H)-quinolinone-4-oxime-O-sulfonic acid compound as claimed in claim 1 wherein R¹ represents a 2-ethylthio-pyridin-3-yl group.

13. A 1-acyl-7-halo-2,3-dihydro-4(1H)-quinolinone-4-oxime-O-sulfonic acid compound as claimed in claim 1 wherein R¹ represents a 3,5-dimethylisoxazol-4-yl group.

14. A 1-acyl-7-halo-2,3-dihydro-4(1H)-quinolinone-4-oxime-O-sulfonic acid compound as claimed in claim 1 wherein R¹ represents a 1,3-benzodioxol-4-yl group.

15. A 1-acyl-7-halo-2,3-dihydro-4(1H)-quinolinone-4-oxime-O-sulfonic acid compound as claimed in claim 1 wherein R¹ represents a quinolin-4-yl group.

16. A 1-acyl-7-halo-2,3-dihydro-4(1H)-quinolinone-4-oxime-O-sulfonic acid compound as claimed in claim 1 wherein R¹ represents a N-methylindol-2-yl group.

17. A pharmaceutical composition comprising a pharmaceutically acceptable carrier and a pharmaceutically effective amount of a 1-acyl-7-halo-2,3-dihydro-4(1H)quinolinone-4-oxime-O-sulfonic acid compound represented by the formula (I):

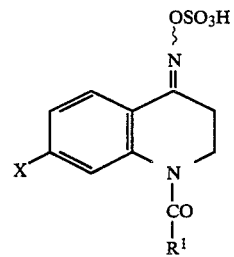

wherein R¹ represents a phenyl group which should be substituted with at least one of an alkylthio group, an amino group which may be substituted with one or two alkyl groups of straight or branched chain having 1 to 4 carbon atoms, a carboxyl group, an aklyloxycarbonyl group of straight or branched chain having 1 to 4 carbon atoms or a phenyl group, or represnts a furyl group, an isoxazolyl group, a pyrrolyl group, a pyridazinyl group, a pyrimidinyl group, a quinolyl gorup, a benzodioxolyl group, a thienyl group, a pyridyl group, an indolyl group or an indenyl group any one of which may be substituted with at least one of an alkyl group of straight or branched chain having 1 to 4 carbon atoms, an alkylthio group, a halogen atom, an amino group which may be substituted with one or two alkyl groups of straight or branched chain having 1 to 4 carbon atoms, a carboxyl group, an alkyloxycarbonyl group of straight or branched chain having 1 to 4 carbon atoms or a phenyl group, provided that when R¹ represents a thienyl group or a pyridyl group, either group should be substituted with at least one of said substituents, X represents a halogen atom, and the bond shown with a wavy line represents a bond of anti-form or syn-form, and a salt thereof as well as a solvate of said compound and a solvate of said salt.

18. A pharmaceutical composition as claimed in claim 17 wherein R¹ represents a N-methylpyrrol-2-yl group.

19. A pharmaceutical composition as claimed in claim 17 wherein $R^1$ represents a furyl group.

20. A pharmaceutical composition as claimed in claim 17 wherein $R^1$ represents a 2,4-dimethylfuran-3-yl group.

21. A pharmaceutical composition as claimed in claim 17 wherein $R^1$ represents a 2-methylthiophen-3-yl group.

22. A pharmaceutical composition as claimed in claim 17 wherein $R^1$ represents a 3-methylthiophen-2-yl group.

23. A pharmaceutical composition as claimed in claim 17 wherein $R^1$ represents a 4-methylthiophen-3-yl group.

24. A pharmaceutical composition as claimed in claim 17 wherein $R^1$ represents a 2-ethylthiophen-3-yl group.

25. A pharmaceutical composition as claimed in claim 17 wherein $R^1$ represents a 2-chlorothiophen-3-yl group.

26. A pharmaceutical composition as claimed in claim 17 wherein $R^1$ represents a 2-methylpyridin-3-yl group.

27. A pharmaceutical composition as claimed in claim 17 wherein $R^1$ represents a 4-methylpyridin-3-yl group.

28. A pharmaceutical composition as claimed in claim 17 wherein $R^1$ represents a 2-ethylthio-pyridin-3-yl group.

29. A pharmaceutical composition as claimed in claim 17 wherein $R^1$ represents a 3,5-dimethylisoxazol-4-yl group.

30. A pharmaceutical composition as claimed in claim 17 wherein $R^1$ represents a 1,3-benzodioxol-4-yl group.

31. A pharmaceutical composition as claimed in claim 17 wherein $R^1$ represents a quinolin-4-yl group.

32. A pharmaceutical composition as claimed in claim 17 wherein $R^1$ represents a N-methylindol-2-yl group.

* * * * *